United States Patent
Chen et al.

(10) Patent No.: US 12,002,251 B2
(45) Date of Patent: Jun. 4, 2024

(54) METHOD FOR INPUTTING IMAGE DISPLAY INFORMATION, METHOD FOR PROCESSING PHYSIOLOGICAL IMAGE INFORMATION, AND EQUIPMENT FOR PROCESSING PHYSIOLOGICAL IMAGE INFORMATION

(71) Applicant: MEIYO MEDICAL TECHNOLOGY INC., Mahé (SC)

(72) Inventors: Hung-Wen Chen, Hsinchu (TW); Chien-Chung Liao, Hsinchu (TW); Hung-Hsiang Ku, New Taipei (TW)

(73) Assignee: MEIYO MEDICAL TECHNOLOGY INC, Mahé (SC)

( * ) Notice: Subject to any disclaimer, the term of this patent is extended or adjusted under 35 U.S.C. 154(b) by 569 days.

(21) Appl. No.: 17/196,328

(22) Filed: Mar. 9, 2021

(65) Prior Publication Data
US 2022/0171983 A1   Jun. 2, 2022

(30) Foreign Application Priority Data
Dec. 2, 2020  (TW) ................... 109142351

(51) Int. Cl.
G06V 10/00 (2022.01)
A61B 5/00 (2006.01)
G06V 10/44 (2022.01)
G09B 19/00 (2006.01)
G16H 30/40 (2018.01)

(52) U.S. Cl.
CPC .......... *G06V 10/443* (2022.01); *A61B 5/0013* (2013.01); *A61B 5/0022* (2013.01); *G09B 19/00* (2013.01); *G16H 30/40* (2018.01)

(58) Field of Classification Search
CPC .... G06V 10/443; G16H 30/40; A61B 5/0013; A61B 5/0022; G09B 19/00
See application file for complete search history.

(56) References Cited

U.S. PATENT DOCUMENTS

| | | | |
|---|---|---|---|
| 2019/0090820 A1* | 3/2019 | Schwenk | A61B 5/721 |
| 2021/0236056 A1* | 8/2021 | Dubin | A61B 7/04 |
| 2021/0382673 A1* | 12/2021 | Van Den Boogaard | A47G 1/02 |
| 2022/0051797 A1* | 2/2022 | Saleh | G16H 50/20 |

FOREIGN PATENT DOCUMENTS

| | | | |
|---|---|---|---|
| CN | 114582484 A | * | 6/2022 |
| TW | 201413634 A | * | 4/2014 |
| TW | 202123255 A | * | 6/2021 |
| TW | 202202123 A | * | 1/2022 |

* cited by examiner

*Primary Examiner* — Khai M Nguyen
(74) *Attorney, Agent, or Firm* — Maschoff Brennan

(57) ABSTRACT

A method for inputting an image display information is provided, and the method comprises: taking a measurement result image of a measuring device to obtain an output image by a camera of a terminal device; transmitting the output image to a cloud server via a communication interface of the terminal device; and recognizing the output image to obtain a recognized matching result related to a recognized measurement value and a recognized measurement unit; and saving the recognized matching result via the cloud server.

19 Claims, 16 Drawing Sheets

METHOD FOR INPUTTING IMAGE DISPLAY INFORMATION, METHOD FOR PROCESSING PHYSIOLOGICAL IMAGE INFORMATION, AND EQUIPMENT FOR PROCESSING PHYSIOLOGICAL IMAGE INFORMATION

CROSS-REFERENCE TO RELATED APPLICATIONS

This non-provisional application claims priority under 35 U.S.C. § 119(a) on Patent Application No(s). 109142351 filed in Republic of China on Dec. 2, 2020, the entire contents of which are hereby incorporated by reference.

BACKGROUND

1. Technical Field

This disclosure relates to a method for processing a measurement value and a measurement unit and an equipment for processing the measurement value and the measurement unit, especially for a method for processing a physiological measurement value and a physiological measurement unit and an equipment for processing the physiological measurement value and the physiological measurement unit.

2. Related Art

Current physiological measurement instruments, such as blood glucose meters, sphygmomanometers, etc., display the actual measurement value and the actual measurement unit on the screen in a digital manner. If a user inputs the actual measurement value to the application program of a terminal device, the actual measurement value is manually inputted to a physiological state application program of the terminal device.

However, when an older user observes the actual measurement value displayed by the physiological measurement instrument and inputs the actual measurement value into the physiological state application program of the terminal device, the older user often inputs an error value into the physiological state application program, which results that the analysis of the physiological state application program lacks credibility. In order to solve the above problems, there are a variety of measurement instruments with Bluetooth communication modules on the market. The Bluetooth communication module is connected to the physiological status application of the terminal device to solve the incorrect observation of the measurement value and incorrect input of the measurement value. However, since the Bluetooth communication protocols of physiological measurement instruments on the market are not consistent, it is necessary to design corresponding application programs to match the measurement instruments with different Bluetooth communication protocols, which results in inconvenience in use.

Therefore, there is indeed a need for an improved equipment for processing image information and an improved method for inputting image display information to improve the above shortcomings.

SUMMARY

Accordingly, this disclosure provides a method for inputting image display information, a method for processing a physiological image information, and an equipment for processing physiological image information, which are applicable to measurement devices with different Bluetooth communication protocols and measurement devices without communication functions. In addition, a user does not require inputting an actual measurement value to the application program of the user's terminal device manually.

According to one or more embodiment of this disclosure, a method for inputting image display information comprises: taking a measurement result image of a measuring device to generate an output image by a camera of a terminal device; transmitting the output image to a cloud server by a communication interface of the terminal device; recognizing the output image to obtain a recognized matching result regarding a recognized measurement value and a recognized measurement unit; and storing the recognized matching result by the cloud server.

According to one or more embodiment of this disclosure, a method for processing physiological image information comprises: taking a measurement result image of a physiological measurement device by a camera of a terminal device to generate an output image; transmitting the output image to a cloud server by a communication interface of the terminal device; recognizing the output image to obtain a recognized matching result regarding a recognized physiological state value and a recognized physiological state unit by the cloud server; transmitting the recognized matching result to the terminal device by the cloud server to generate a confirmed matching result regarding a confirmed physiological state value and a confirmed physiological state unit; transmitting the confirmed matching result to the cloud server by the terminal device; and storing the confirmed matching result by the cloud server.

According to one or more embodiment of this disclosure, an equipment for processing image information comprises a terminal device and a cloud server, the terminal device comprises a camera and a communication interface electrically connected to the camera, the camera is configured to photograph a measurement result image of a measurement device to generate an output image, the cloud server is electrically connected to the communication interface, the cloud server is configured to recognize the output image to obtain a recognized matching result regarding a recognized measurement value and a recognized measurement unit, and the cloud server stores the recognized matching result and transmitting the recognized matching result to the terminal device.

In view of the above description, since the recognized measurement value and the recognized measurement unit stored in the terminal device can be used as the input basis for the application program of the terminal device, which can be applicable to measurement devices with different Bluetooth communication protocols and measurement devices without communication functions. In addition, the incorrect observation of the measurement value and incorrect input of the measurement value can be avoided, and it is more efficient and easy to use the measurement device.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
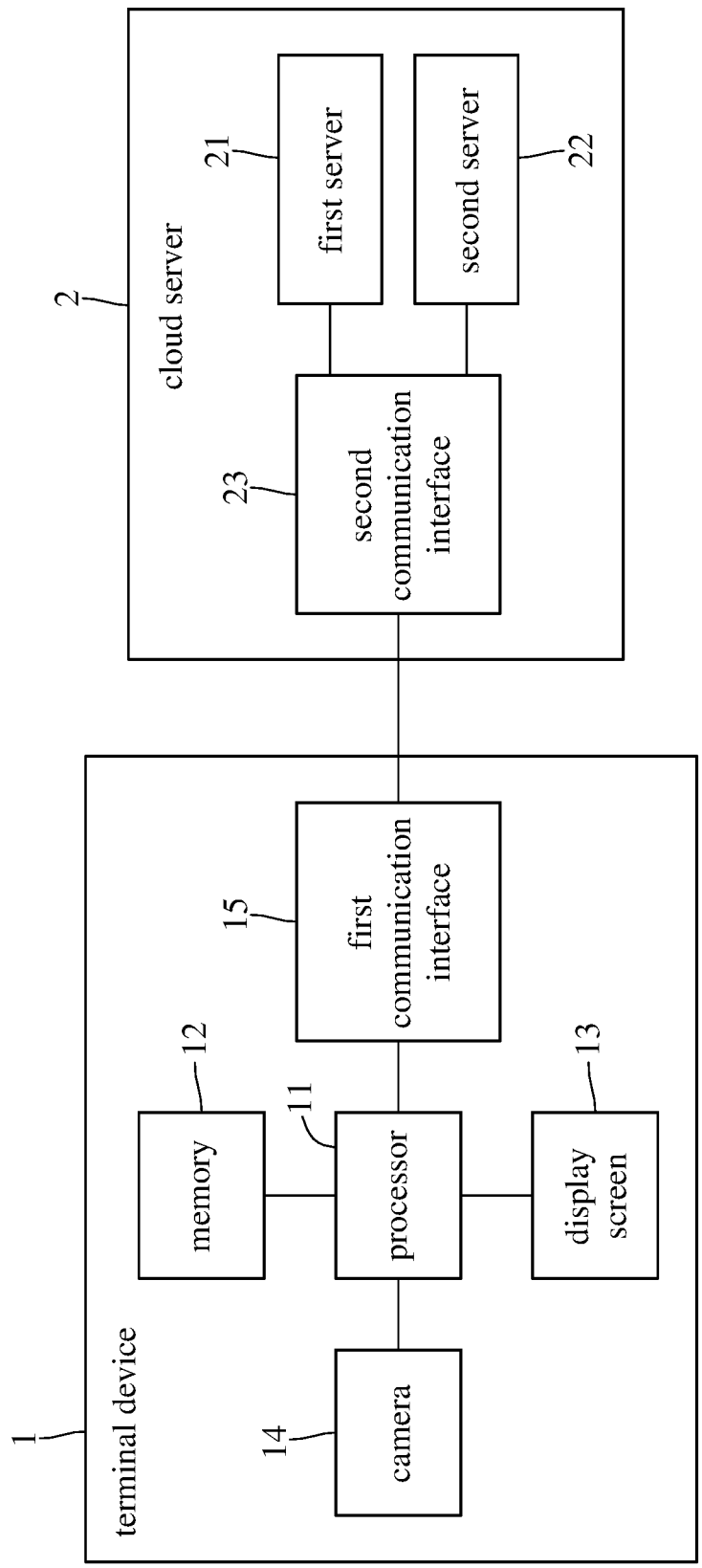
FIG. 1 is a block diagram of an embodiment of an equipment for processing image information of this disclosure.

FIG. 1 is a block diagram of an embodiment of an equipment for processing image information of this disclosure. Refer to FIG. 1, the equipment for processing image information comprises a terminal device 1 and a cloud server 2. For example, the terminal device 1 can be a computer host or a mobile communication device, and the terminal device 1 is communicated with the cloud server 2. The terminal device 1 comprises a processor 11, a memory 12, a display screen 13, a camera 14, and a first communication interface 15. The processor 11 is electrically connected to the memory 12, the display screen 13, the camera 14 and the first communication interface 15. The display screen 13 is electrically connected to the camera 14 through the processor 11, the first communication interface 15 is electrically connected to the camera 14 through the processor 11, and the memory 12 stores application programs, such as web programs, computer applications, or mobile applications (APP).

The cloud server 2 comprises a first server 21, a second server 22, and a second communication interface 23. The first server 21 is electrically connected to the second communication interface 23, and the second server 22 is electrically connected to the second communication interface 23, and the second communication interface 23 is electrically connected to the first communication interface 15. In one embodiment, each of the first communication interface 15 and the second communication interface 23 is a circuit interface for communicating with the network. Therefore, the first communication interface 15 of the terminal device 1 and the second communication interface 23 of the cloud server 2 can transmit and receive signals and data each other via the network.

Figure 2:
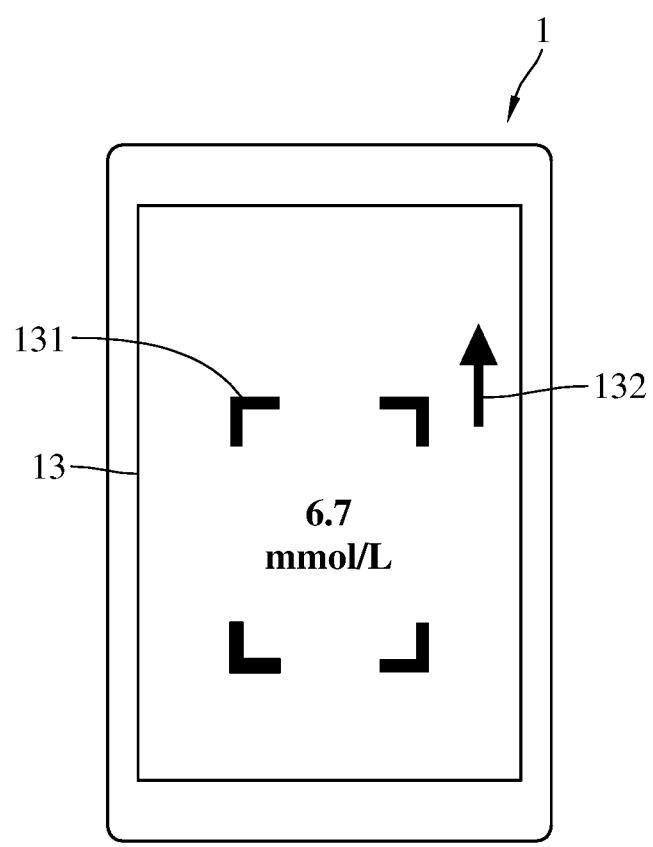
FIG. 2 is a schematic diagram of a display screen of FIG. 1 showing a measurement result image.

FIG. 2 is a schematic diagram of the display screen 13 of FIG. 1 showing a measurement result image. The display screen 13 is configured to display a frame 131 and a direction indicator 132, the measurement result image is displayed in the frame 131, and the direction indicator 132 is outside the frame 131. The direction indicator 132 permanently face toward the same direction. The direction indicator 132 guides the user to adjust the shooting angle of the camera 14 so that the measurement result image of the measurement device is presented in the frame 131 at the correct angle. The processor 11 drives the camera 14 to shoot the measurement result image presented in the frame 131 and generates an initial image. The processor 11 first performs an image processing for the initial image to generate an output image. For example, the image processing can be grayscale conversation, edge detection or a combination of grayscale conversation and edge detection. Then the first communication interface 15 transmits the output image to the second communication interface 23 of the cloud server 2. The cloud server 2 obtains the output image via the second communication interface 23. Alternatively, the initial image is directly used as an output image and the processor 11 does not perform the image processing for the initial image. In other embodiments, when the display screen 13 does not display at least one of the frame 131 and the direction indicator 132, the user can also use the camera 14 to shoot the measurement result image displayed by the measurement device to obtain the initial image.

The cloud server 2 recognizes the output image from the terminal device 1 to obtain a recognized matching result regarding a recognized measurement value and a recognized measurement unit, and the cloud server 2 stores the recognized matching result and transmits the recognized matching result to the processor 11 of the terminal device 1 through the second communication interface 23. The recognized matching result is stored in the memory 12 by the processor 11, and the recognized matching result can be used as the input basis of the application program.

The measurement result image of the measurement device may have an actual measurement value, or the measurement result image may have the actual measurement value and at least one of a feature pattern (such as a heart-shaped pattern, a thermometer pattern, or a footprint pattern), an actual measurement unit and a brand pattern of the measurement device. The feature pattern can correspond to the actual measurement value, for example, the heart-shaped pattern can correspond to the actual measurement value of the heart rate, the thermometer pattern can correspond to the actual measurement value of the body temperature or air temperature, and the footprint pattern can correspond to the actual measurement value of the walk step. The type of measurement device is not limited. For example, the measurement device is a physiological measurement device, and the actual measurement value and the actual measurement unit displayed by the physiological measurement device are the actual physiological state value and the actual physiological state unit respectively.

Figure 3:
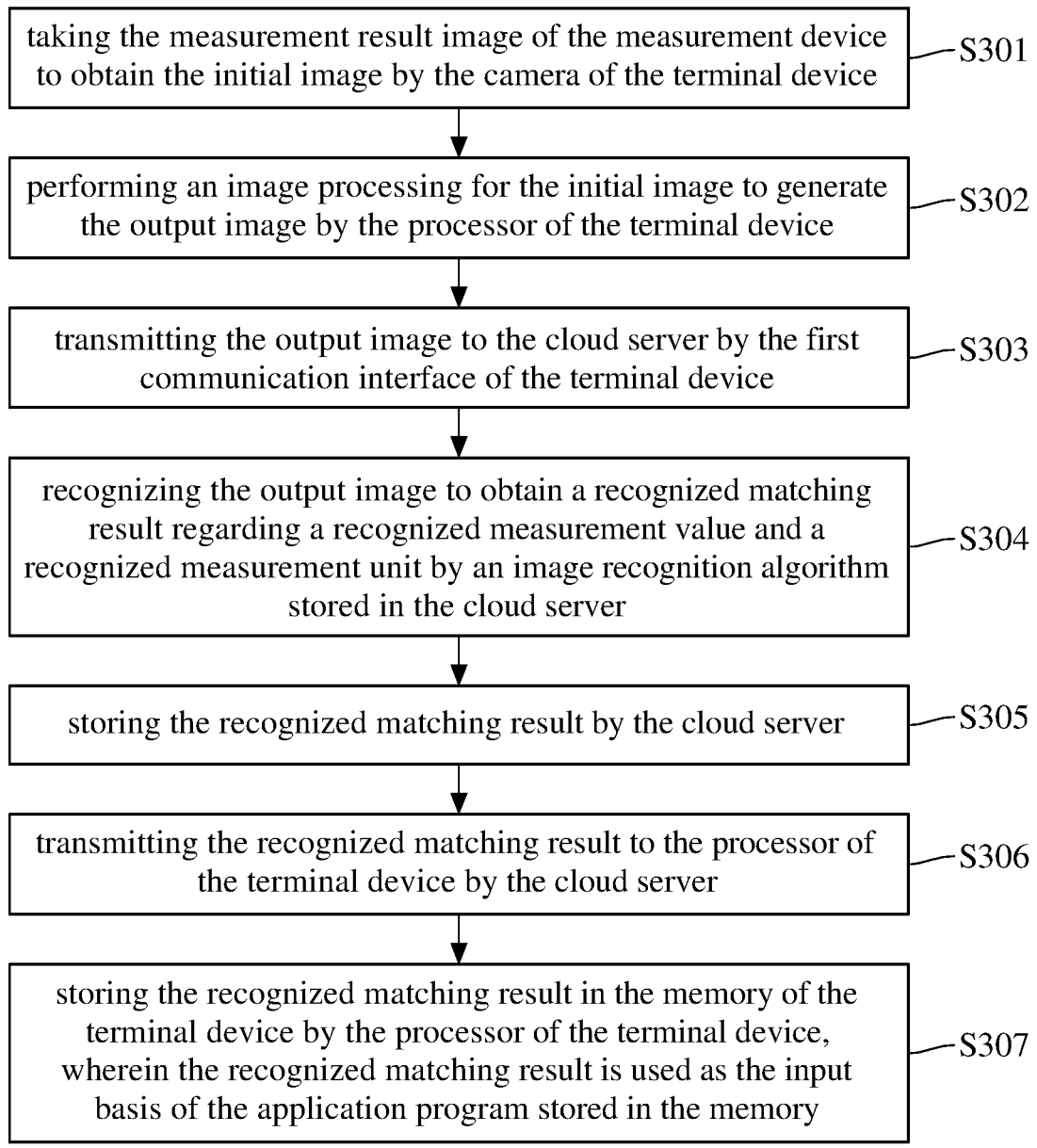
FIG. 3 is a flowchart of the first embodiment of a method for inputting image display information of this disclosure.

FIG. 3 is a flowchart of the first embodiment of a method for inputting image display information of this disclosure. The method in FIG. 3 can be implemented by any type of an image processing equipment. Specifically, when the camera 14 of the image processing equipment obtains the initial image, the display screen 13 of the image processing equipment does not display at least one of the frame 131 and the direction indicator 132, or the display screen 13 of the image processing equipment displays the frame 131 and the direction indicator 132. For the convenience of the subsequent disclosure, the image processing equipment in FIG. 1, as an example, may perform the method for inputting image display information in ways shown as the following embodiments.

Refer to FIG. 3, First, the camera 14 of the terminal device 1 shoots the measurement result image of the measurement device to generate an output image, which includes steps S301 and S302. Step S301 is taking the measurement result image of the measurement device to obtain the initial image by the camera 14 of the terminal device 1. The memory 12 stores image processing programs (such as grayscale conversion and edge detection), and step S302 is performing an image processing (such as grayscale conversion, edge detection, or a combination of grayscale conversation and edge detection) for the initial image to generate the output image by the processor 11 of the terminal device 1, and the data size of the output image is less than the data size of the initial image. Step S303 is transmitting the output image to the cloud server 2 by the first communication interface 15 of the terminal device 1. The cloud server 2 stores an image recognition algorithm, such as a machine learning algorithm or an optical character recognition algorithm. Step S304 is recognizing the output image to obtain a recognized matching result regarding a recognized measurement value and a recognized measurement unit by an image recognition algorithm stored in the cloud server 2. Step S305 is storing the recognized matching result by the cloud server 2. Step S306 is transmitting the recognized matching result to the processor 11 of the terminal device 1 by the cloud server 2. Step S307 is storing the recognized matching result in the memory 12 of the terminal device 1 by the processor 11 of the terminal device 1. The recognized matching result is used as the input basis of the application program stored in the memory 12. Thereby, the user can use the terminal device 1 to confirm whether the recognized measurement value and the recognized measurement unit are the same as the actual measurement value and the actual measurement unit respectively.

Regarding other embodiments of the method for inputting the image display information, the terminal device 1 may directly use the initial image as the output image without performing any image processing on the initial image, and send the initial image to the cloud server 2, and then the cloud server 2 recognizes the initial image to obtain the recognized matching result regarding the recognized measurement value and the recognized measurement unit.

Figure 4:
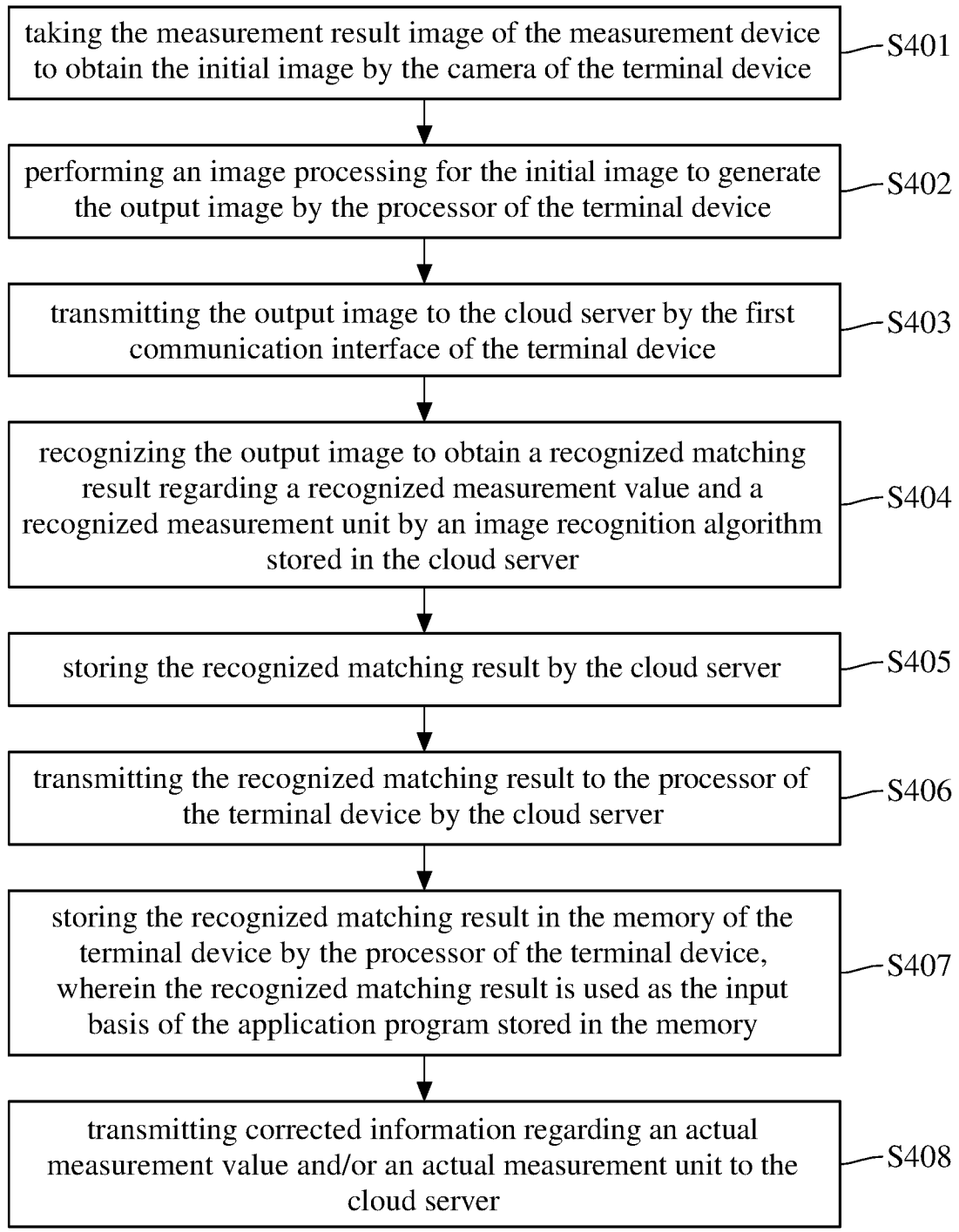
FIG. 4 is a flowchart of the second embodiment of a method for inputting image display information of this disclosure.

FIG. 4 is a flowchart of the second embodiment of a method for inputting image display information of this disclosure. Steps S401 to S407 of FIG. 4 are respectively the same as steps S301 to S307 of FIG. 3, and the difference between the second embodiment and the first embodiment is step S408. As shown in FIG. 4, step S408 is transmitting corrected information regarding an actual measurement value or/and an actual measurement unit to the cloud server 2 after storing the recognized matching result in the memory 12 by the processor 11. Specifically, when the recognized measurement value or the recognized measurement unit obtained by the terminal device 1 is different from the actual measurement value or the actual measurement unit of the measurement result image of the measurement device, the terminal device 1 transmits the corrected information regarding the actual measurement value or/and the actual measurement unit to the cloud server 2. The image recognition algorithm stored in the cloud server 2 can be updated based on the corrected information. The updated image recognition algorithm can improve image recognition accuracy.

Figure 5:
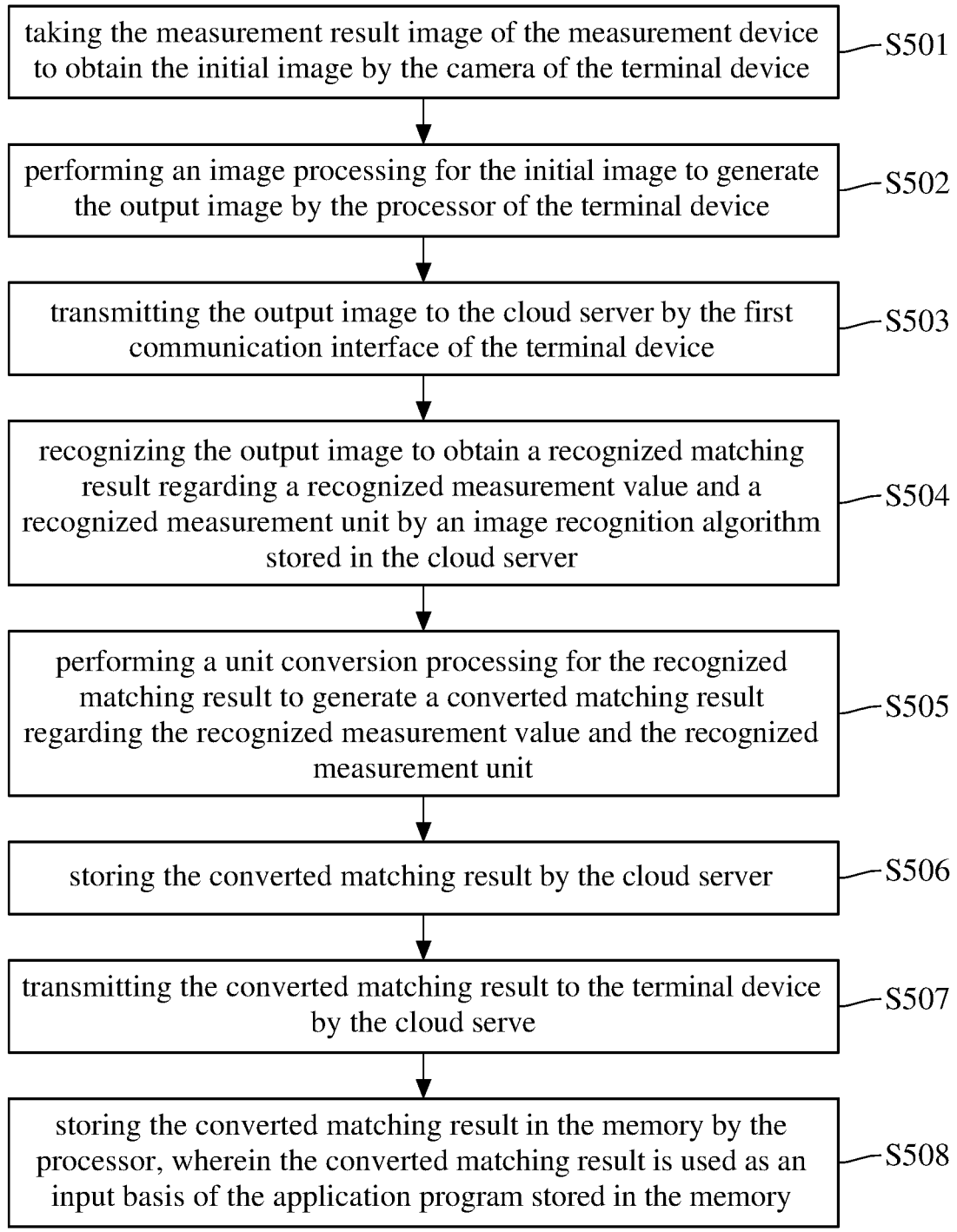
FIG. 5 is a flowchart of the third embodiment of a method for inputting image display information of this disclosure.

FIG. 5 is a flowchart of the third embodiment of a method for inputting image display information of this disclosure. Steps S501 to S504 of FIG. 5 are respectively the same as steps S301 to S304 of FIG. 3, and the differences between the third embodiment and the first embodiment comprise steps S505 to S508. As shown in FIG. 5, step S505 is performing a unit conversion processing for the recognized matching result to generate a converted matching result after obtaining the recognized matching result regarding the recognized measurement value and the recognized measurement unit by the cloud server 2. Step S506 is storing the converted matching result by the cloud server 2. Step S507 is transmitting the converted matching result to the terminal device 1 by the cloud server 2. Step S508 is storing the converted matching result in the memory 12 by the processor 11, and the converted matching result is used as the input basis of the application program stored in the memory 12. Specifically, the blood glucose can be represented by two different units, one of the unit is milligram/deciliter (mg/dl), the other unit is millimole/liter (mmol/L), the conversion formula for the two units is: mg/dl÷18=mmol/L or mmol/L×18=mg/dl. Since users in different countries may use different measurement units, the cloud server 2 performs the unit conversion processing for the recognized matching result, which allows the users in different countries to easily use the converted matching result as the input basis of the application program stored in the memory 12. In addition, the cloud server 2 can also store the recognized matching result and the converted matching result, and transmit the recognized matching result and the converted matching result to the terminal device 1. The user can use the terminal device 1 to confirm whether the recognized measurement value and the recognized measurement unit are the same as the actual measurement value and the actual measurement unit respectively and know the measurement results based on his accustomed measurement unit, so it can provide better user experience for the user of the terminal device 1.

Figure 6:
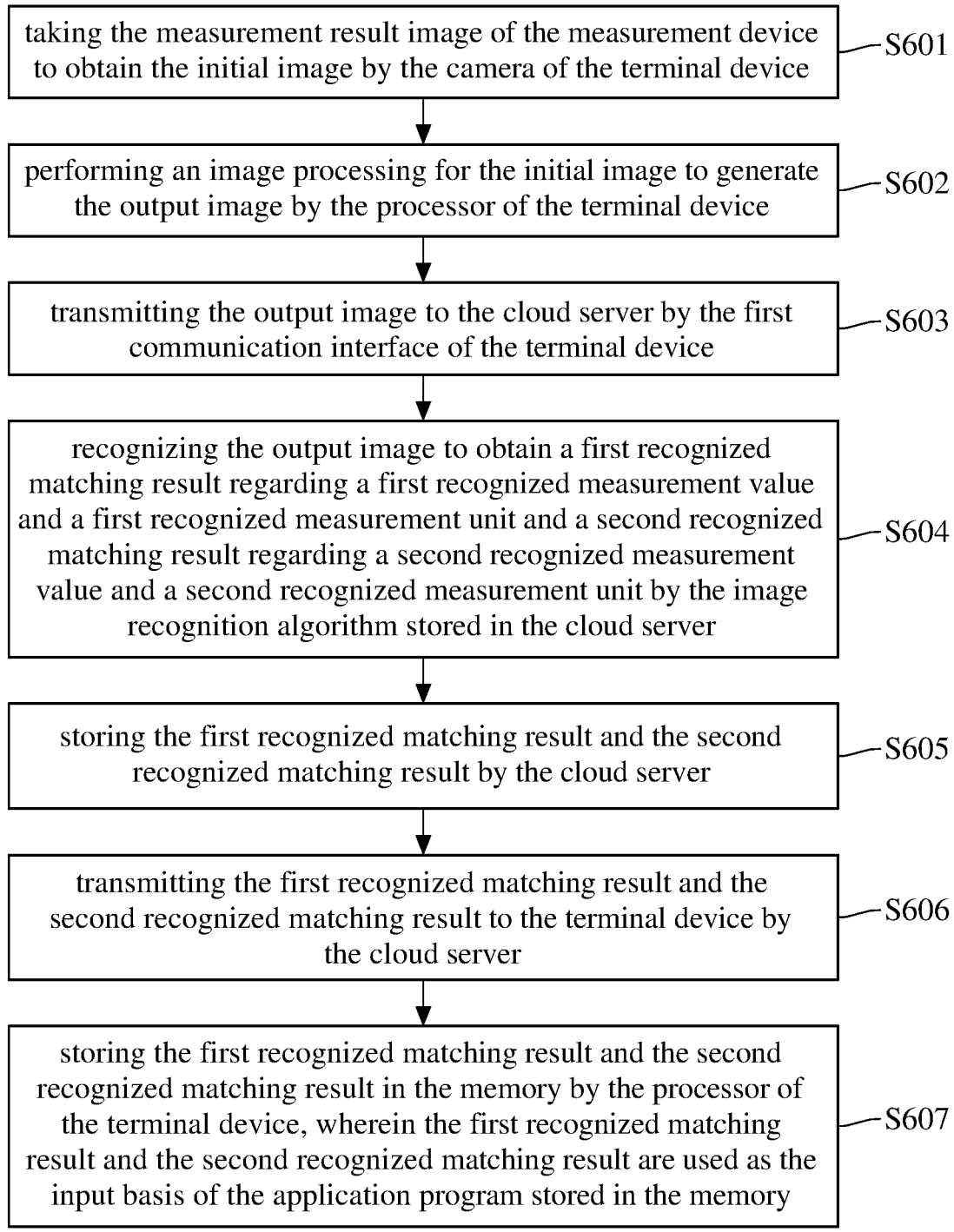
FIG. 6 is a flowchart of the fourth embodiment of a method for inputting image display information of this disclosure.

FIG. 6 is a flowchart of the fourth embodiment of a method for inputting image display information of this disclosure. Steps S601 to S603 of FIG. 6 are respectively the same as steps S301 to S303 of FIG. 3, and the differences between the fourth embodiment and the first embodiment comprise steps S604 to S607. As shown in FIG. 6, step S604 is recognizing the output image to obtain a first recognized matching result regarding a first recognized measurement value and a first recognized measurement unit and a second recognized matching result regarding a second recognized measurement value and a second recognized measurement unit by the image recognition algorithm stored in the cloud server 2. Specifically, the output image from the terminal device 1 includes two different actual measurement values and two actual measurement units corresponding to the actual measurement values respectively. Step S605 is storing the first recognized matching result and the second recognized matching result by the cloud server 2. Step S606 is transmitting the first recognized matching result and the second recognized matching result to the terminal device 1 by the cloud server 2. Step S607 is storing the first recognized matching result and the second recognized matching result in the memory 12 by the processor 11 of the terminal device 1, and the first recognized matching result and the second recognized matching result are used as the input basis of the application program stored in the memory 12.

In addition, step S604 can also be replaced by recognizing the output image to obtain the first recognized matching result regarding the first recognized measurement value and the recognized measurement unit and the second recognized matching result regarding the second recognized measurement value and the recognized measurement unit by the image recognition algorithm stored in the cloud server 2. For example, the measurement device can be a sphygmomanometer, and the output image from the terminal device 1 includes a systolic blood pressure and a diastolic blood pressure.

Figure 7:
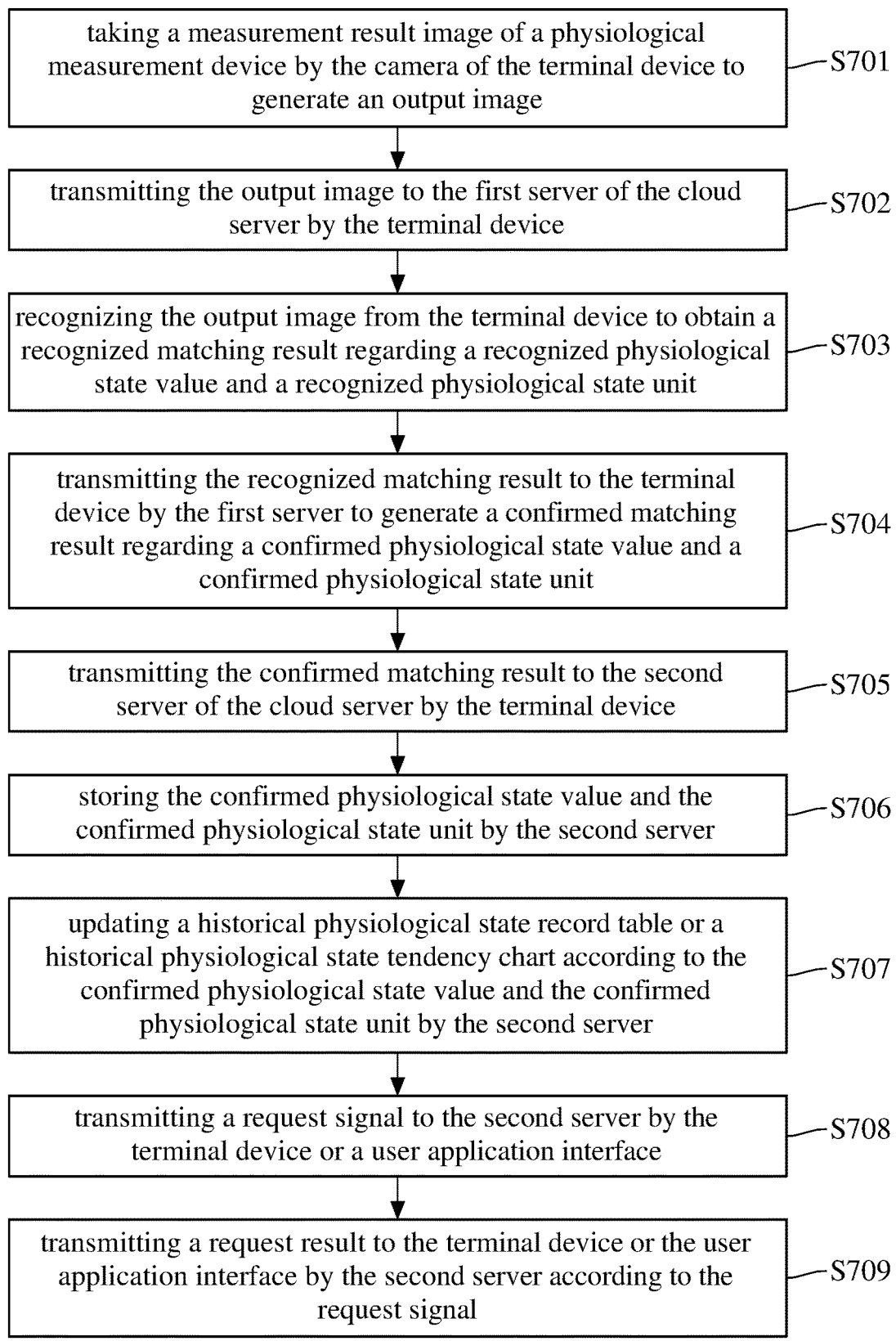
FIG. 7 is a flowchart of the first embodiment of a method for processing physiological image information of this disclosure.

FIG. 7 is a flowchart of the first embodiment of a method for processing physiological image information of this disclosure. The physiological image information processing method shown in FIG. 7 can be executed by different types of image processing equipment, but is preferably executed by the equipment shown in FIG. 1 for processing the image information. The equipment shown in FIG. 1 for processing image information, as an example, performs the following embodiments of the method for processing physiological image information.

As shown in FIG. 7, step S701 is taking a measurement result image of a physiological measurement device by the camera 14 of the terminal device 1 to generate an output image. Step S702 is transmitting the output image to the first server 21 of the cloud server 2 by the terminal device 1, and the first server 21 stores the image recognition algorithm. Step S703 is recognizing the output image from the terminal device 1 to obtain a recognized matching result regarding a recognized physiological state value and a recognized physiological state unit by the first server 21. Step S704 is storing the recognized matching result by the first server 21 and transmitting the recognized matching result to the terminal device 1 by the first server 21 to generate a confirmed matching result regarding a confirmed physiological state value and a confirmed physiological state unit. Specifically, the terminal device 1 receives the recognized matching result from the first server 21 of the cloud server 2, and the recognized matching result can be used as the input basis of the application program stored in the terminal device 1, and the user can use the terminal device 1 to confirm whether the recognized physiological state value and the recognized physiological state unit are the same as the actual physiological state value and the actual physiological state unit respectively to generate the confirmed matching result, which can improve the accuracy of the confirmed matching result. Step S705 is transmitting the confirmed matching result to the second server 22 of the cloud server 2 by the terminal device 1, and then storing the confirmed matching result by the second server 22, wherein storing the confirmed matching result by the second server 22 includes steps S706 and S707. Step S706 is storing the confirmed physiological state value and the confirmed physiological state unit by the second server 22. Step S707 is updating a historical physiological state record table or a historical physiological state tendency chart according to the confirmed physiological state value and the confirmed physiological state unit by the second server 22. The historical physiological state record table and the historical physiological state tendency chart have been stored in the second server 22 of the cloud server 2 in advance. Either the historical physiological state record table or the historical physiological state tendency chart includes multiple historical physiological states. Moreover, the confirmed matching result can be used as the corrected information by the terminal device 1 and the terminal device 1 transmits the confirmed matching result to the first server 21 of the cloud server 2 to update the image recognition algorithm. The updated image recognition algorithm can improve image recognition accuracy.

As shown in FIG. 7, step S708 is transmitting a request signal to the second server 22 by the terminal device 1 or a user application interface. For example, the user application interface may be a mobile communication device or a computer host of a relative, friend, doctor, case manager, or nursing staff of the user of the terminal device 1 or may be a computer host of a hospital. Step S709 is transmitting a request result to the terminal device 1 or the user application interface by the second server 22 according to the request signal, wherein the request result can be the confirmed matching result, the updated historical physiological state record table, or the updated historical physiological state tendency chart. Specifically, the terminal device 1 and the user application interface are installed with an authorized program (such as a remote medical care program or a remote physiological monitoring program) to transmit the request signals to the second server 22, wherein the authorized program is an application program authorized by the cloud server 2. The authorized program can transmit information to the cloud server 2, and the authorized program is set by the second server 22 of the cloud server 2. Simply speaking, the terminal device 1 or the user application interface can use the authorized program to transmit the request signal to the second server 22 of the cloud server 2. In other embodiments, the second server 22 of the cloud server 2 may further perform a unit conversion processing for the confirmed matching result to obtain and store a converted confirmed matching result. After the terminal device 1 or the user application interface transmits the request signal to the cloud server 2, the terminal device 1 or the user application interface can obtain a request result from the cloud server 2, wherein the request result further includes the confirmed conversion matching result, so that users in different countries can easily know the measurement result after obtaining the request result.

Figure 8:
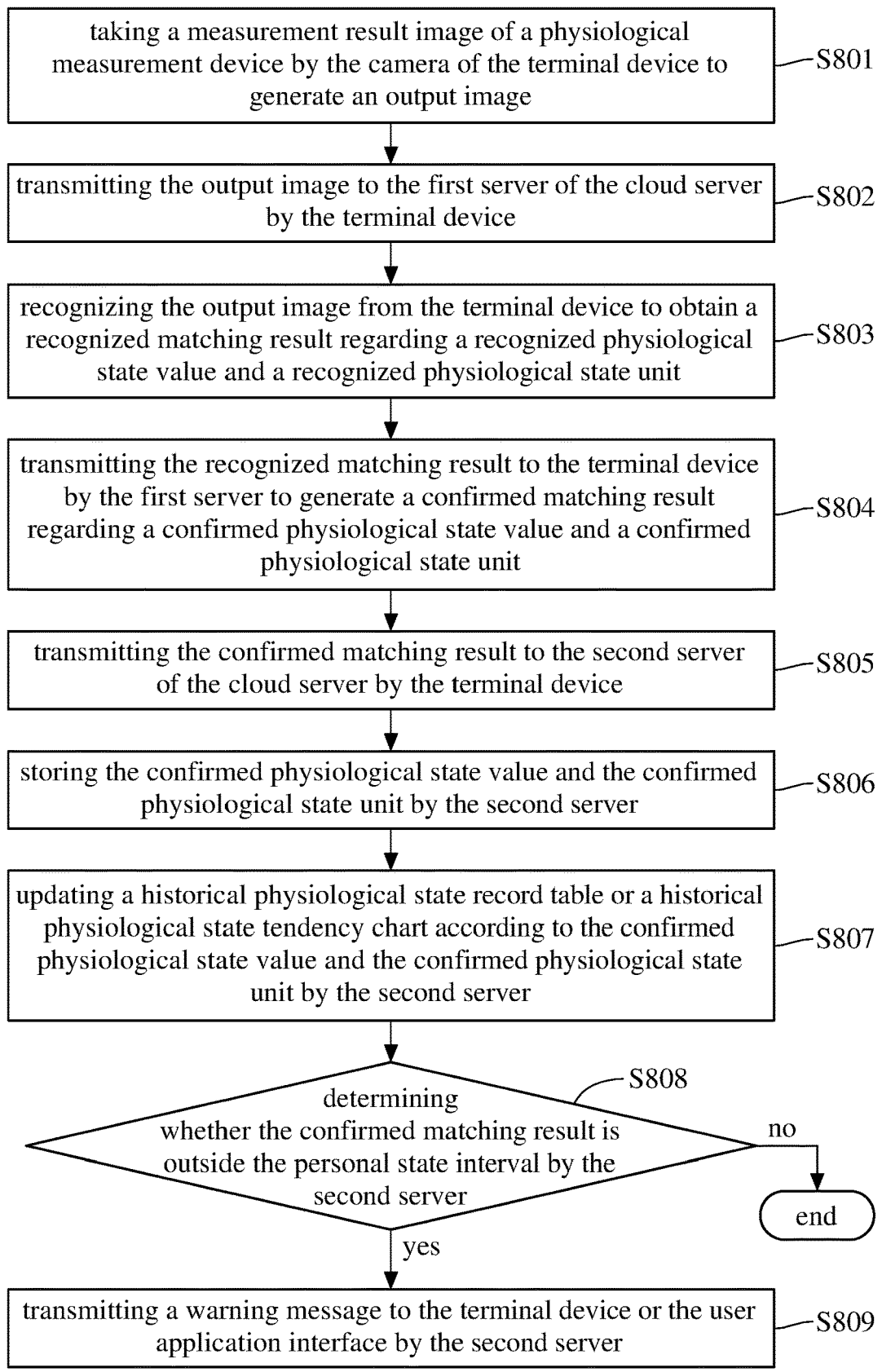
FIG. 8 is a flowchart of the second embodiment of a method for processing physiological image information of this disclosure.

FIG. 8 is a flowchart of the second embodiment of a method for processing physiological image information of this disclosure. Steps S801 to S807 are respectively the same as steps S701 to S707, and the differences between the embodiment of FIG. 8 and the embodiment of FIG. 7 comprise steps S808 and S809. Simply speaking, the second server 22 can determine whether a physiological state information is outside a personal state interval, and transmit a warning message to the terminal device 1 or the user application interface when the physiological state information is outside the personal state interval. Wherein the personal state interval is related to the physiological state of the user using the terminal device 1, and the physiological state information may be, for example, the confirmed matching result, the confirmed conversion matching result, the updated historical physiological state record table, or the updated historical physiological state tendency chart. As shown in FIG. 8, when the physiological state information is the confirmed matching result, step S808 is determining whether the confirmed matching result is outside the personal state interval by the second server 22. When the second server 22 of the cloud server 2 determines that the confirmed matching result is outside the personal status interval, step S809 is performed. Step S809 is transmitting a warning message to the terminal device 1 or the user application interface by the second server 22 of the cloud server 2, wherein a user who can obtain the warning message by the user application interface may be different from another user who can transmit the request signal by the user application interface shown in step S708 of FIG. 7. It is worth mentioning that the user who can obtain the warning message by the user application interface is listed in a white list stored in the second server 22 of the cloud server 2, and a user of the terminal device 1 can use the terminal device 1 to set the white list in the second server 22. In addition, the user application interface of the user who can obtain the warning message has an application program associated with the user who can obtain the warning message, so that the user who can obtain the warning message can obtain the warning message by an authorized program, text message, or voice call. When the second server 22 of the cloud server 2 determines that the confirmed matching result is not outside the personal status interval, the method for processing physiological image information is finished. Specifically, the personal state interval is an interval in which the user's physiological state value is in a healthy state, so the personal state interval may vary with age, height, weight, daily routine, medication record, or medical history of a user using terminal device 1. For example, the personal state interval is the user's normal blood pressure interval, and the normal blood pressure interval varies with the user's age or the personal status interval is the user's normal blood glucose interval, and the normal blood glucose interval before a meal is different from the normal blood glucose interval after the meal.

Figure 9:
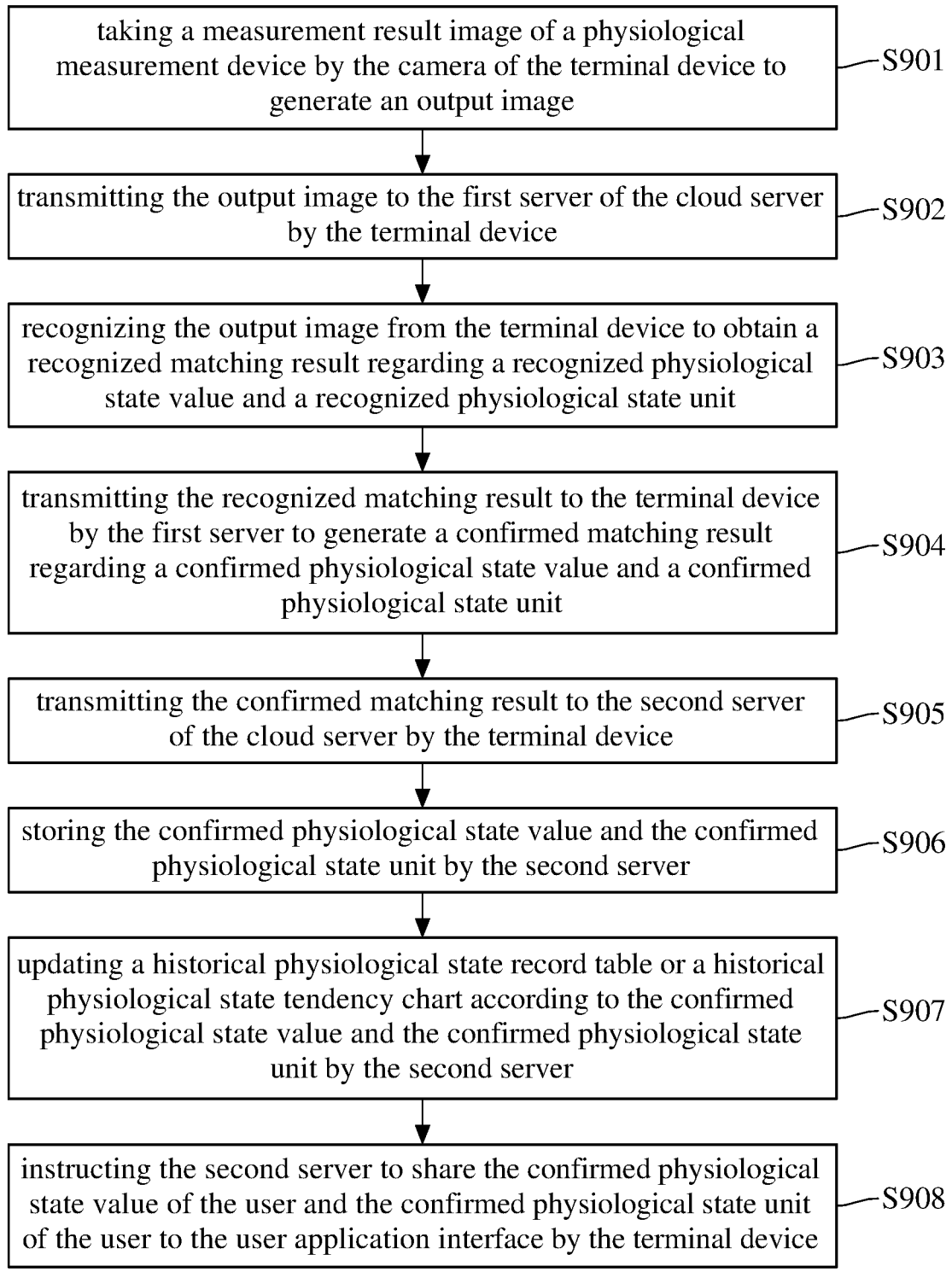
FIG. 9 is a flowchart of the third embodiment of a method for processing physiological image information of this disclosure.

FIG. 9 is a flowchart of the third embodiment of a method for processing physiological image information of this disclosure. Steps S901 to S907 are respectively the same as steps S701 to S707, and the difference between the embodiment of FIG. 9 and the embodiment of FIG. 7 comprises step S908. Simply speaking, the terminal device 1 may instruct the second server 22 to share the sharing information to the user application interface, wherein the sharing information may be the physiological state information. In addition, the user application interface of the user who can obtain the sharing information has an authorized program associated with the user who can obtain the sharing information. As shown in FIG. 9, when the sharing message comprises the confirmed physiological state value and the confirmed physiological state unit, step S908 is instructing the second server 22 to share the confirmed physiological state value and the confirmed physiological state unit of the user of the terminal device 1 to the user application interface by the terminal device 1, wherein the user who can obtain the confirmed physiological state value and the confirmed physiological state unit which are shared by the user of the terminal device 1 by the user application interface may be different from the user who can transmit the request signal by the user application interface (shown in step S708 of FIG. 7) or the user who can obtain the warning message by the user application interface. It is worth mentioning that the user who can obtain the sharing information by the user application interface is listed in a white list stored in the second server 22 of the cloud server 2, and the user of the terminal device 1 can use the terminal device 1 to set the white list in the second server 22.

Figure 10:
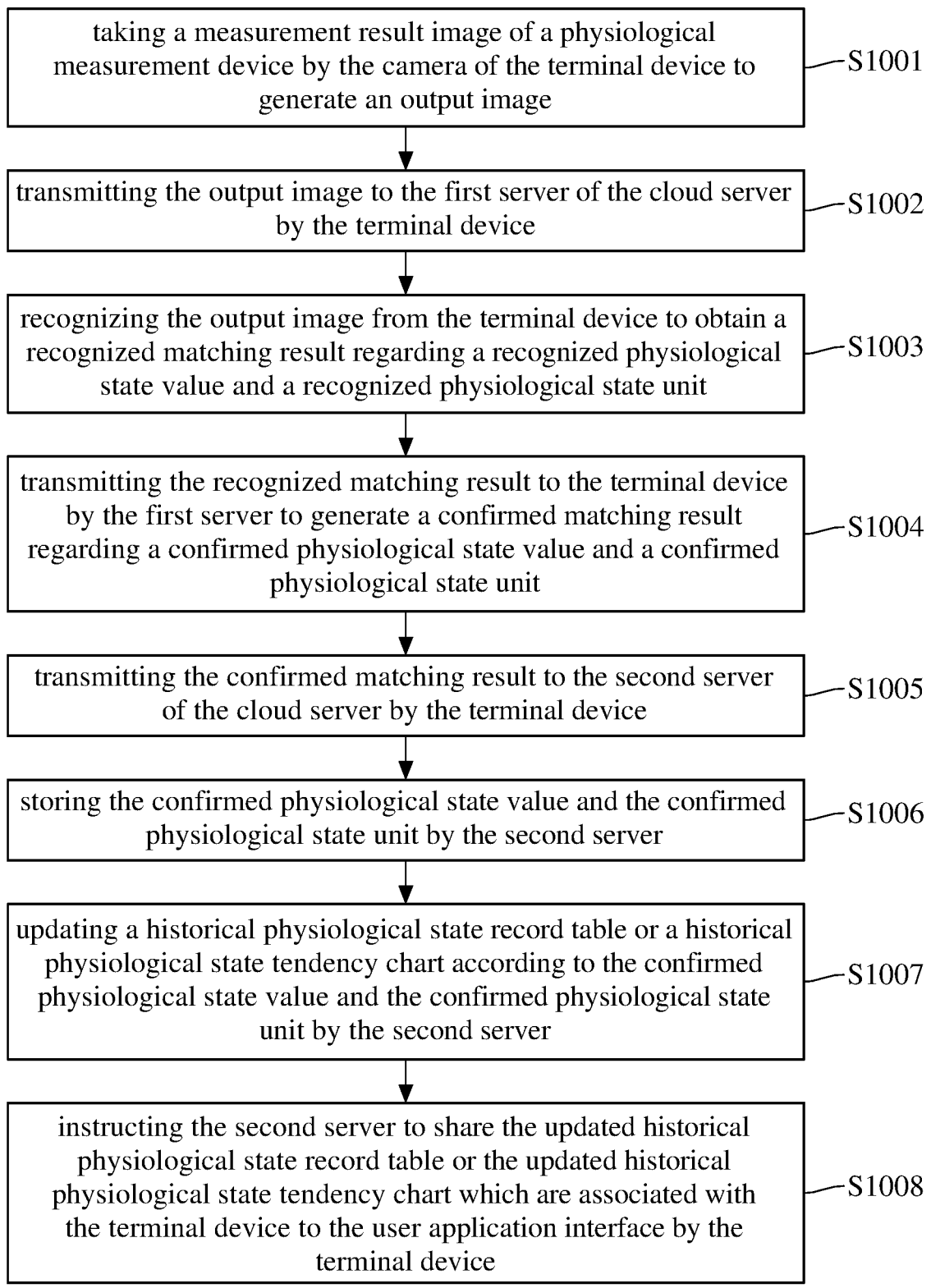
FIG. 10 is a flowchart of the fourth embodiment of a method for processing physiological image information of this disclosure.

FIG. 10 is a flowchart of the fourth embodiment of a method for processing physiological image information of this disclosure. Steps S1001 to S1007 of FIG. 10 are respectively the same as steps S701 to S707 of FIG. 7, and the difference between the embodiment of FIG. 10 and the embodiment of FIG. 7 comprises step S1008. When the sharing information is the updated historical physiological state record table or the updated historical physiological state tendency chart, step S1008 is instructing the second server 22 to share the updated historical physiological state record table or the updated historical physiological state tendency chart which are associated with the terminal device 1 to the user application interface by the terminal device 1, wherein the updated historical physiological state record table or the updated historical physiological state tendency chart includes the current physiological state value of the user using the terminal device 1 and multiple historical physiological state values of the user using the terminal device 1. In addition, the user of the terminal device 1 can also share a historical physiological state record table or historical physiological state tendency chart within a specified time period, that is, the sharing information can also be physiological state information within the specified time period.

Figure 11A:
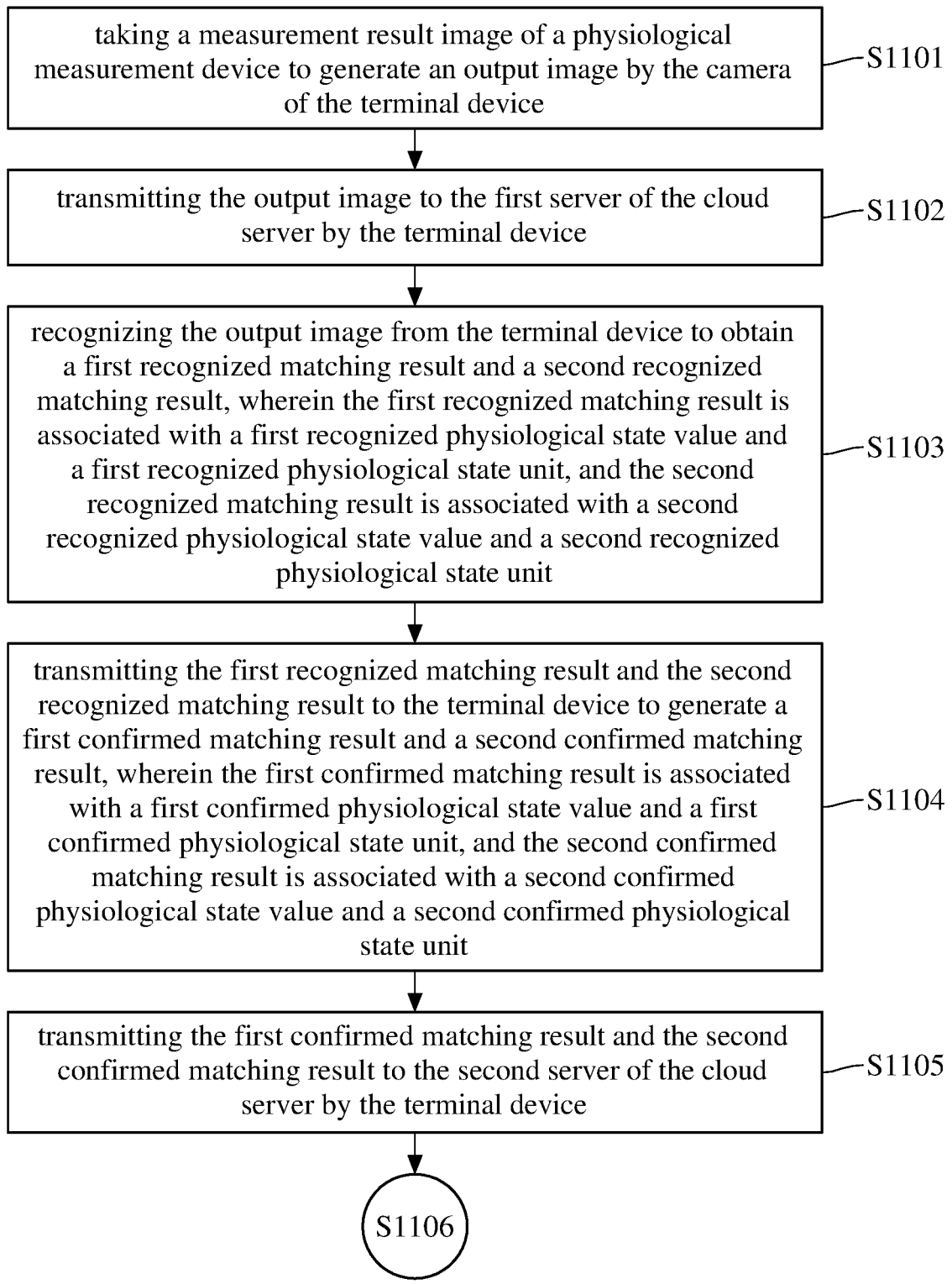
FIGS. 11A and 11B are flowcharts of the fifth embodiment of a method for processing physiological image information of this disclosure.
Figure 11B:
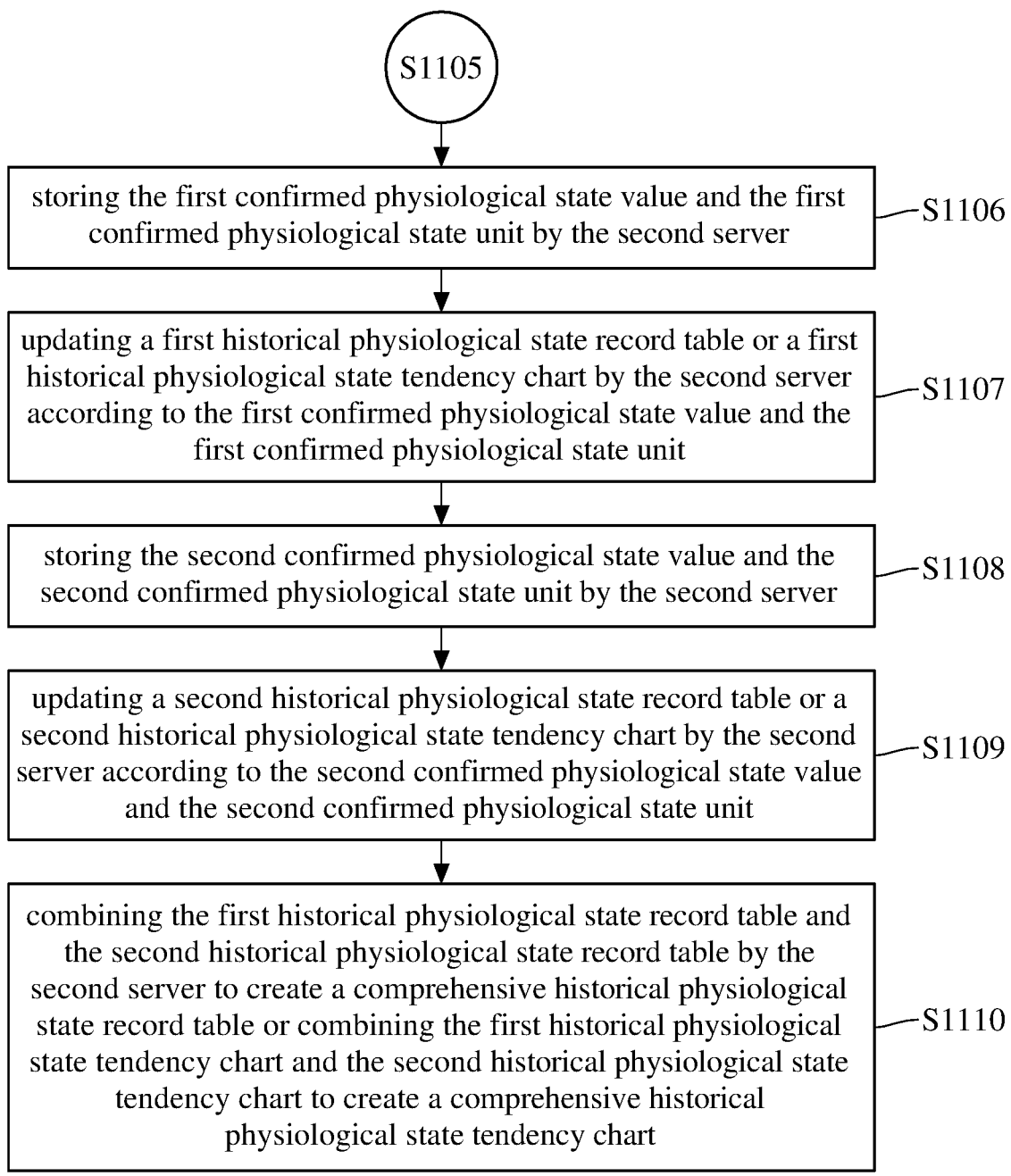

FIGS. 11A and 11B are flowcharts of the fifth embodiment of a method for processing physiological image information of this disclosure. As shown in FIGS. 11A and 11B, step S1101 is taking a measurement result image of a physiological measurement device to generate an output image by the camera 14 of the terminal device 1. Step S1102 is transmitting the output image to the first server 21 of the cloud server 2 by the terminal device 1. Step S1103 is recognizing the output image from the terminal device 1 to obtain a first recognized matching result and a second recognized matching result, wherein the first recognized matching result is associated with a first recognized physiological state value and a first recognized physiological state unit, the second recognized matching result is associated with a second recognized physiological state value and a second recognized physiological state unit, the first recognized physiological state value is different from the second recognized physiological state value, and the first recognized physiological state unit is different from the second recognized physiological state unit. Specifically, the output image from the terminal device 1 contains more than one actual physiological state values and actual physiological state units. Therefore, the output image can be identified by the cloud server 2 to generate more than one recognized physiological state values and recognized physiological state units. Step S1104 is storing the first recognized matching result and the second recognized matching result by the first server 21 and transmitting the first recognized matching result and the second recognized matching result to the terminal device 1 by the first server 21 to generate a first confirmed matching result and a second confirmed matching result, wherein the first confirmed matching result is associated with a first confirmed physiological state value and a first confirmed physiological state unit, and the second confirmed matching result is associated with a second confirmed physiological state value and a second confirmed physiological state unit, wherein the first server 21 may simultaneously transmit the first recognized matching result and the second recognized matching result to the terminal device 1, or the first server 21 may respectively transmit the first recognized matching result and the second recognized matching result to the terminal device at two different time points. Specifically, the terminal device 1 receives the first recognized matching result and the second recognized matching result from the first server 21 of the cloud server 2, and uses them as the input basis of the application program in the terminal device 1. The user of the terminal device 1 confirms whether the first recognized matching result and the second recognized matching result are correct to generate the first confirmed matching result and the second confirmed matching result, which can improve the accuracies of the first confirmed matching result and the second confirmed matching result. Step S1105 is transmitting the first confirmed matching result and the second confirmed matching result to the second server 22 of the cloud server 2 by the terminal device 1, and then the second server 22 stores the first confirmed matching result and the second confirmed matching result, wherein storing the first confirmed matching result by the second server 22 includes step S1106 and step S1107. Step S1106 is storing the first confirmed physiological state value and the first confirmed physiological state unit by the second server 22, and step S1107 is updating a first historical physiological state record table or a first historical physiological state tendency chart by the second server 22 according to the first confirmed physiological state value and the first confirmed physiological state unit, wherein the first historical physiological state record table and the first historical physiological state tendency chart have been previously stored in the second server 22, and either the first historical physiological state record table or the first historical physiological state tendency chart includes multiple first historical physiological state values. In other embodiments, the first recognized physiological state unit may be the same as the second recognized physiological state unit.

As shown in FIGS. 11A and 11B, storing the second confirmed matching result by the second server 22 includes step S1108 and step S1109. Step S1108 is storing the second confirmed physiological state value and the second confirmed physiological state unit by the second server 22, and step S1109 is updating a second historical physiological state record table or a second historical physiological state tendency chart by the second server 22 according to the second confirmed physiological state value and the second confirmed physiological state unit, wherein the second historical physiological state record table and the second historical physiological state tendency chart have been previously stored in the second server 22, and either the second historical physiological state record table or the second historical physiological state tendency chart includes multiple second historical physiological state values. Next, step S1110 is combining the first historical physiological state record table and the second historical physiological state record table by the second server 22 to create a comprehensive historical physiological state record table or combining the first historical physiological state tendency chart and the second historical physiological state tendency chart to create a comprehensive historical physiological state tendency chart. Specifically, after the terminal device 1 or the user application interface sends the request signal to the cloud server 2, the request result that can be obtained from the cloud server 2 includes the first confirmed matching result, the second confirmed matching result, the updated first historical physiological state record sheet, the updated first historical physiological state tendency chart, the updated second historical physiological state record sheet, the updated second historical physiological state tendency chart, the comprehensive historical physiological state record sheet, the comprehensive history physiological state tendency chart or any combination of the above. In other embodiments, the second server 22 of the cloud server 2 may further perform a unit conversion processing for the first confirmed matching result and the second confirmed matching result to obtain and store a first converted confirmed matching result and a second converted confirmed matching result. After the terminal device 1 or the user application interface sends the request signal to the cloud server 2, the request result that can be obtained from the cloud server 2 may further include the first converted confirmed matching result, the second converted confirmed matching result or a combination thereof.

Figure 12:
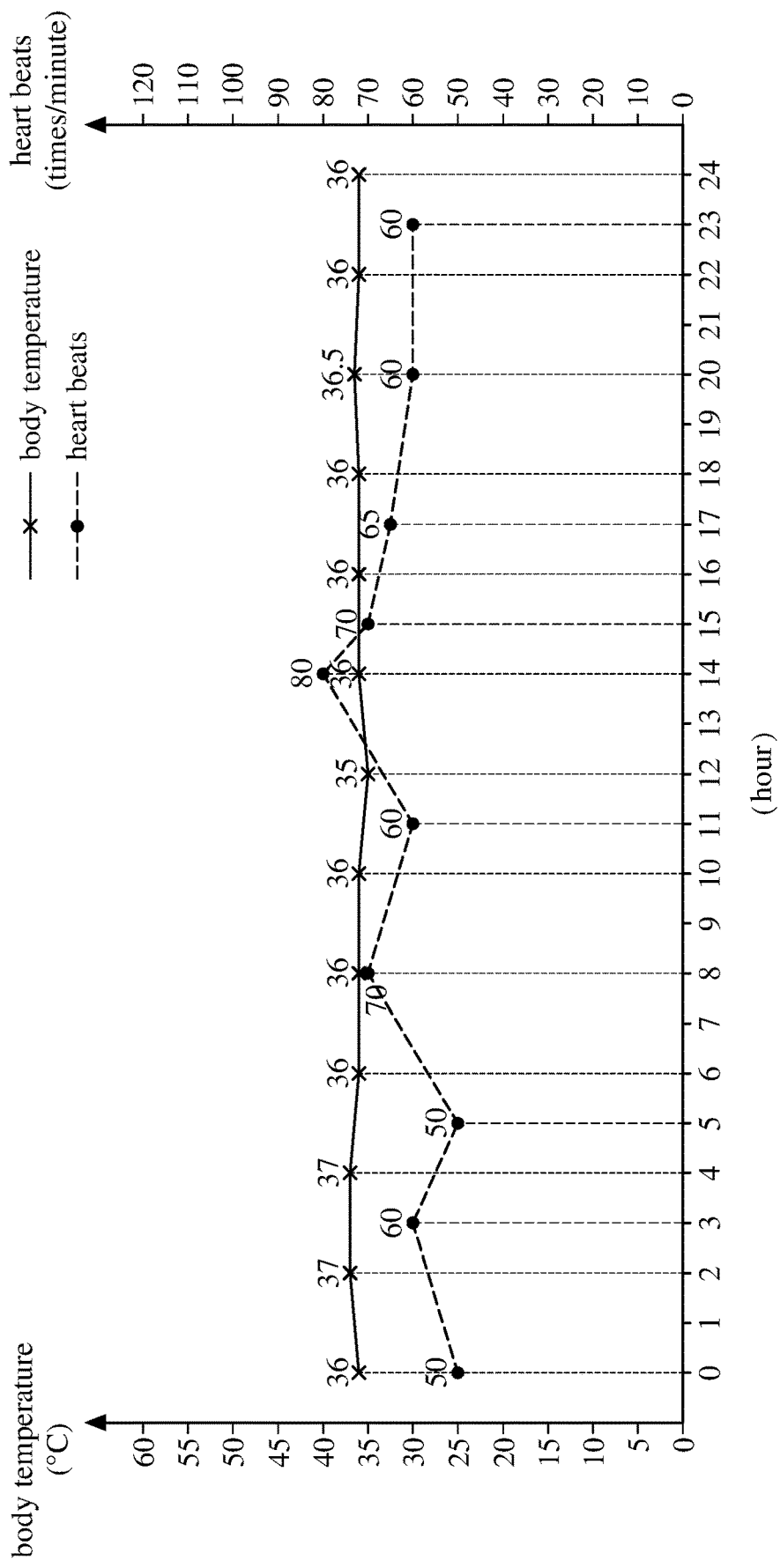
FIG. 12 is one embodiment of a comprehensive historical physiological state tendency chart.

FIG. 12 is one embodiment of a comprehensive historical physiological state tendency chart. As shown in FIG. 12, the unit of the horizontal axis is hour, the unit of the first vertical axis is Celsius, and the unit of the second vertical axis is times/minute. The first historical physiological state value indicates the body temperature of the user of the terminal device 1, and the second historical physiological state value indicates the number of heart beats per minute of the user of the terminal device 1. For example, a doctor can obtain a comprehensive historical physiological state tendency chart of the user of the terminal device 1 from the cloud server 2 by a computer host of a hospital, and use the comprehensive historical physiological state tendency chart of the user of the terminal device 1 as an important basis for evaluating the physiological state of the user of the terminal device 1. The above historical physiological state values and historical physiological state units are only examples and the present invention are not only limited to the above historical physiological state values and historical physiological state units.

Figure 13A:
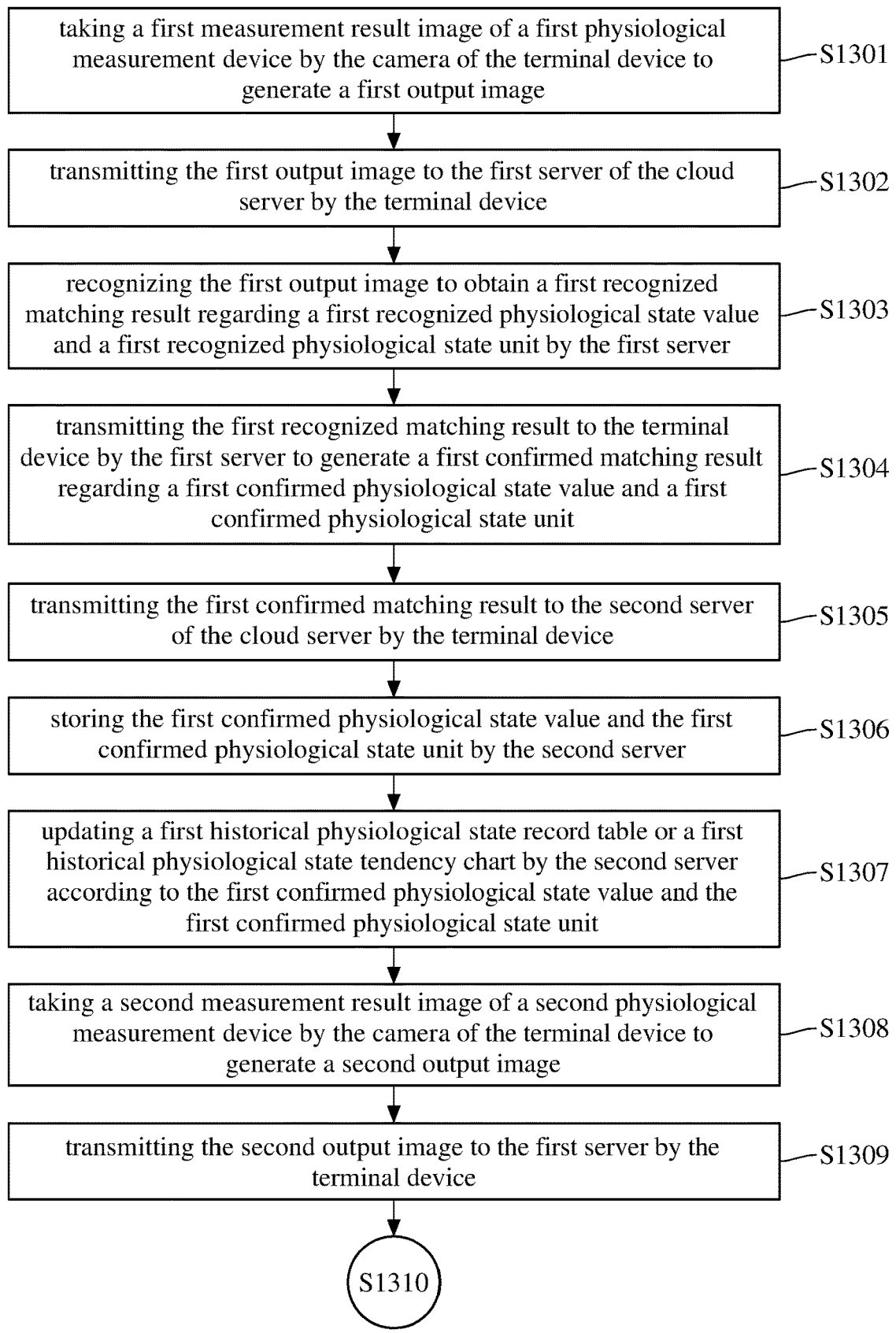
FIGS. 13A and 13B are flowcharts of the sixth embodiment of a method for processing physiological image information of this disclosure.
Figure 13B:
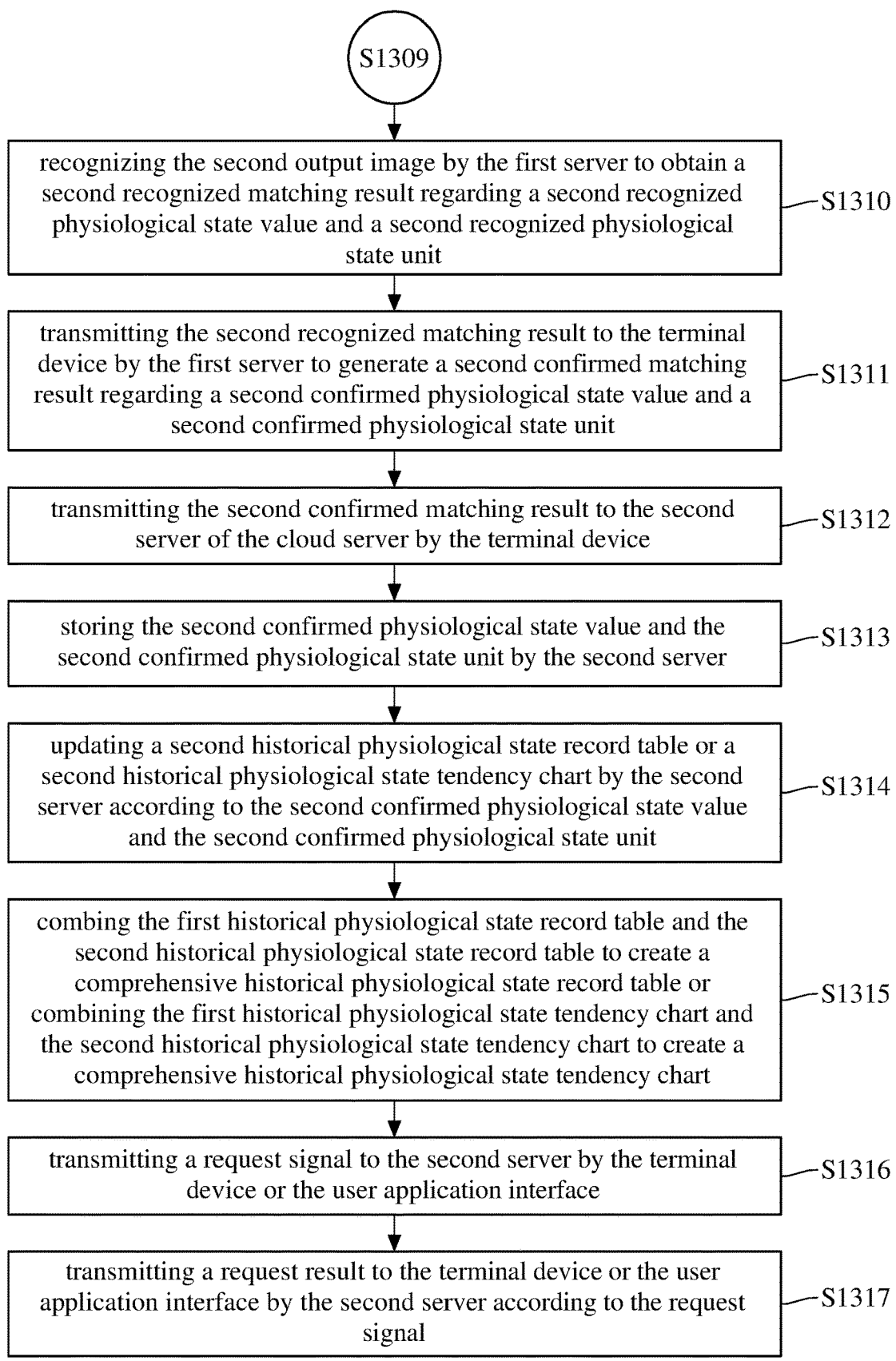

FIGS. 13A and 13B are flowcharts of the sixth embodiment of a method for processing physiological image information of this disclosure. As shown in FIGS. 13A and 13B. Step S1301 is taking a first measurement result image of a first physiological measurement device by the camera 14 of the terminal device 1 to generate a first output image. Step S1302 is transmitting the first output image to the first server 21 of the cloud server 2 by the terminal device 1. Step S1303 is recognizing the first output image to obtain a first recognized matching result regarding a first recognized physiological state value and a first recognized physiological state unit by the first server 21. Step S1304 is storing and transmitting the first recognized matching result to the terminal device 1 by the first server 21 to generate a first confirmed matching result regarding a first confirmed physiological state value and a first confirmed physiological state unit, wherein the first recognized matching result can be used as the input basis of the application program in the memory 12 and the application program in the memory 12 can be, for example, an authorized program. Specifically, the terminal device 1 can input the first recognized matching result into the application program to generate the first confirmed matching result. The user of the terminal device 1 can determine whether the first recognized physiological state value and the first recognized physiological state unit are respectively the same as the first actual physiological state value and the first actual physiological state unit, which are displayed at the first measurement result image of the first physiological measurement device. When the first recognized physiological state value and the first recognized physiological state unit are the same as the first actual physiological state value and the first actual physiological state unit, the first recognized physiological state value and the first recognized physiological state unit can be used as the first confirmed physiological state value and the first confirmed physiological state unit to generate the first confirmed matching result. When the first recognized physiological state value and the first recognized physiological state unit are different from the first actual physiological state value and the first actual physiological state unit, the user of the terminal device 1 can modify the first recognized physiological state value and the first recognized physiological state unit according to the first actual physiological state value and the first actual physiological state unit to generate the first confirmed matching result regarding the first confirmed physiological state value and the first confirmed physiological state unit. Step S1305 is transmitting the first confirmed matching result to the second server 22 of the cloud server 2 by the terminal device 1, and the second server 22 stores the first confirmed matching result, wherein storing the first confirmed matching result by the second server 22 includes step S1306 and step S1307. Step S1306 is storing the first confirmed physiological state value and the first confirmed physiological state unit by the second server 22, and step S1307 is updating a first historical physiological state record table or a first historical physiological state tendency chart by the second server 22 according to the first confirmed physiological state value and the first confirmed physiological state unit.

Step S1308 is taking a second measurement result image of a second physiological measurement device by the camera 14 of the terminal device 1 to generate a second output image. Step S1309 is transmitting the second output image to the first server 21 by the terminal device 1. Step S1310 is recognizing the second output image by the first server 21 to obtain a second recognized matching result regarding a second recognized physiological state value and a second recognized physiological state unit. Step S1311 is transmitting the second recognized matching result to the terminal device 1 by the first server 21 to generate a second confirmed matching result regarding a second confirmed physiological state value and a second confirmed physiological state unit, wherein the second recognized matching result can be used as the input basis of the application program in the memory 12 and the application program in the memory 12 can be, for example, an authorized program. Specifically, the terminal device 1 can input the second recognized matching result into the application program to generate the second confirmed matching result. The user of the terminal device 1 can determine whether the second recognized physiological state value and the second recognized physiological state unit are respectively the same as a second actual physiological state value and a second actual physical state unit displayed on a second measurement result image of a second physiological measurement device. When the second recognized physiological state value and the second recognized physiological state unit are respectively the same as the second actual physiological state value and the second actual physiological state unit, the second recognized physiological state value and the second recognized physiological state unit can be used as the second confirmed physiological state value and the second confirmed physiological state unit to generate the second confirmed matching result. When the second recognized physiological state value and the second recognized physiological state unit are different from the second actual physiological state value and the second actual physiological state unit, the user of the terminal device 1 can modify the second recognized physiological state value and the second recognized physiological state unit according to the second actual physiological state value and the second actual physiological state unit to generate the second confirmed matching result regarding the second confirmed physiological state value and the second confirmed physiological state unit.

Step S1312 is transmitting the second confirmed matching result to the second server 22 of the cloud server 2 by the terminal device 1, and then the second server 22 stores the second confirmed matching result, wherein storing the second confirmed matching result by the second server 22 includes step S1313 and step S1314. Step S1313 is storing the second confirmed physiological state value and the second confirmed physiological state unit by the second server 22, and step S1314 is updating a second historical physiological state record table or a second historical physiological state tendency chart by the second server 22 according to the second confirmed physiological state value and the second confirmed physiological state unit. Next, step S1315 is combing the first historical physiological state record table and the second historical physiological state record table to create a comprehensive historical physiological state record table or combining the first historical physiological state tendency chart and the second historical physiological state tendency chart to create a comprehensive historical physiological state tendency chart. Then, step S1316 is transmitting a request signal to the second server 22 by the terminal device 1 or the user application interface, and step S1317 is transmitting a request result to the terminal device 1 or the user application interface by the second server 22 according to the request signal. Specifically, in the embodiment of FIGS. 13A and 13B, the camera 14 of the terminal device 1 shoots two different physiological measurement devices at two different time points to obtain two measurement result images of the two different time points. It is worth mentioning that when the first recognized matching result is different from the first actual physiological state value and the first actual physiological state unit, or the second recognized matching result is different from the second actual physiological state value and the second actual physiological state unit, the first confirmed matching result or the second confirmed matching result can be used as corrected information and the terminal device 1 can send the first confirmed matching result or the second confirmed matching result to the first server 21 of the cloud server 2 to update the image recognition algorithm. The updated image recognition algorithm can improve image recognition accuracy.

Figure 14:
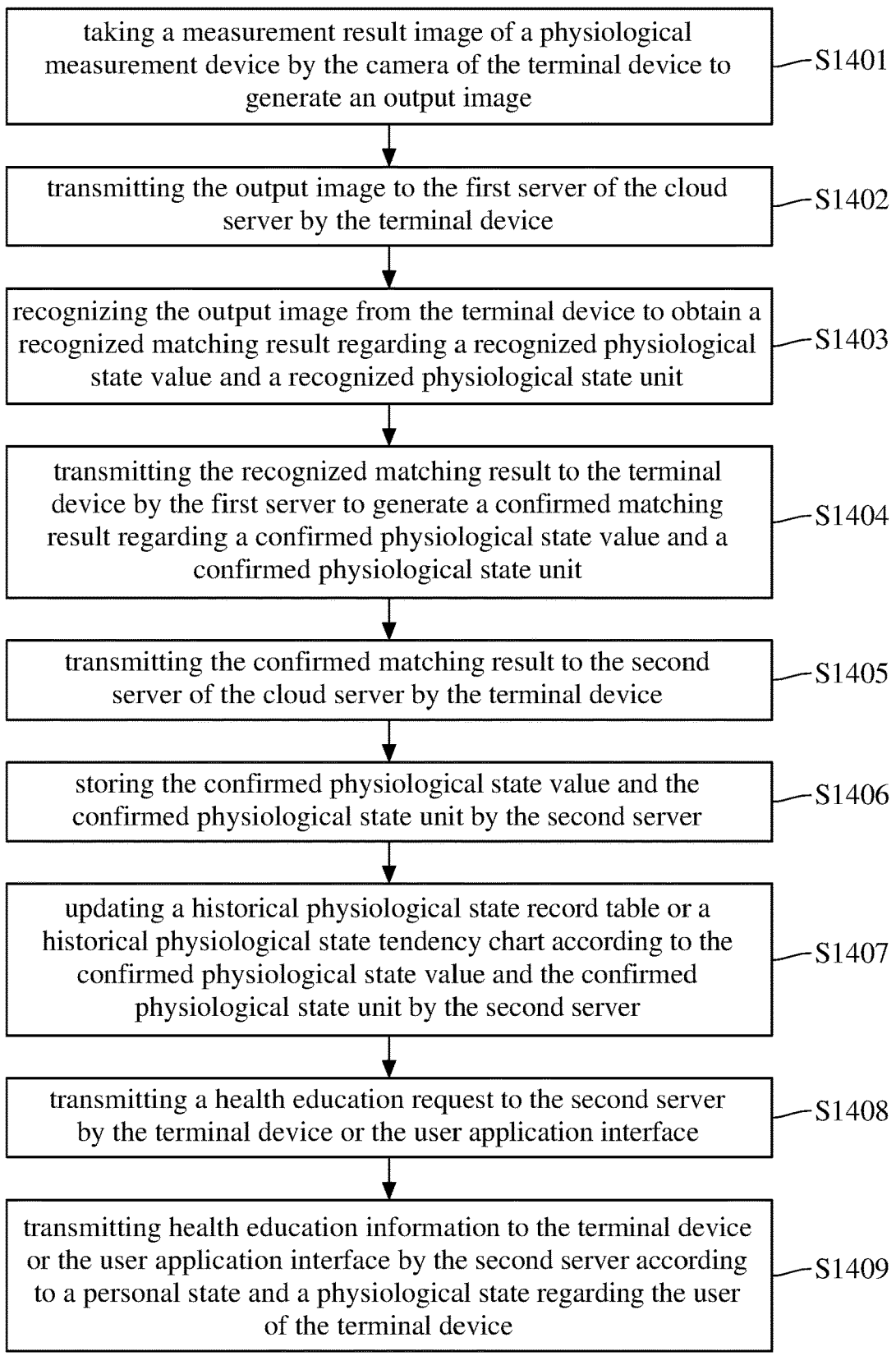
FIG. 14 is a flowchart of the seventh embodiment of a method for processing physiological image information of this disclosure.

FIG. 14 is a flowchart of the seventh embodiment of a method for processing physiological image information of this disclosure. Steps S1401 to S1407 of FIG. 14 are respectively the same as steps S701 to S707 of FIG. 7, and the difference between the embodiment of FIG. 14 and the embodiment of FIG. 7 comprises steps S1408 and S1409. As shown in FIG. 14, step S1408 is transmitting a health education request to the second server 22 by the terminal device 1 or the user application interface after updating the historical physiological state record table or the historical physiological state tendency chart by the second server 22 of the cloud server 2. Step S1409 is transmitting health education information to the terminal device 1 or the user application interface by the second server 22 according to a personal state and a physiological state regarding the user of the terminal device 1. It is worth mentioning that users who can obtain health education information are listed in a white list, and the user of the terminal device 1 uses the terminal device 1 to set the white list in the second server 22 of the cloud server 2. In another embodiment after receiving the confirmed matching result or updating the historical physiological state record table or the historical physiological state tendency chart, the second server 22 can directly provide health education information to the terminal device 1 and the users who can reverie the health education Information. In addition, in another embodiment, after the terminal device 1 or the user application interface obtains the sharing message, the warning message, or the request result, the terminal device 1 or the user application interface transmits the health education request to the second server 22 according to the sharing message, the warning message or the request result, and the second server 22 transmits health education information to the terminal device 1 or the user application interface according to the health education request.

In other embodiments, when the cloud server 2 has stored multiple historical physiological state values of the user of the terminal device 1 within a time period, the user application interface may send a request signal to the second server 22, and the second server 22 transmits the request result to the user application interface according to the request signal from the user application interface. The request result received by the user application interface includes multiple historical physiological state values of the user of the terminal device 1 in the time period. Then, the user of the user application interface (e.g., medical staff) can provide health education information according to received historical physiological state values and send the health education information to the terminal device 1 through the second server 22. In other words, when the user of the user application interface is a medical staff, the user of the user application interface can provide health education information according to the request result obtained by the user, and send the health education information to the terminal device 1 through the second server 22.

In view of the above description, the recognized measurement value and the recognized measurement unit stored in the terminal device 1 can be used as the input basis of the application program of the terminal device 1. This disclosure can help avoiding wrong input of the measurement value. It can also be applied to measuring instruments with different Bluetooth communication protocols or measuring devices without communication function, making it more efficient and easy to use. In addition, the user of the terminal device 1 can adjust diet and daily routine according to the health education information sent by the cloud server 2 to improve the personal health status continuously. The user's relatives, friends or doctors in the hospital can increase their attention to the user's health status according to the warning message and sharing physiological state information sent by the cloud server 2. Furthermore, the doctors in the hospital can obtain the user's current physiological state value, updated historical physiological state record table, updated historical physiological state tendency chart, comprehensive historical physiological state record table or comprehensive historical physiological state tendency chart from the cloud server 2, and can provide suitable health education information to the user's terminal device, which help user to improve his health status based on provided health education information.

What is claimed is:

1. A method for inputting image display information, comprising:
    taking a measurement result image of a measuring device to generate an output image by a camera of a terminal device;
    transmitting the output image to a cloud server by a communication interface of the terminal device;
    recognizing the output image to obtain a recognized matching result having a recognized measurement value and a recognized measurement unit;
    storing the recognized matching result by the cloud server; and
    comparing physiological state information and a personal state interval by the cloud server, and transmitting a warning message to the terminal device or a user application interface by the cloud server when the physiological state information is outside the personal state interval, wherein the personal state interval is related to daily routine, medication record, or medical history of a user.

2. The method according to claim 1, wherein taking the measurement result image of the measurement device by the camera of the terminal device to generate the output image comprises:
    taking the measurement result image to obtain an initial image; and
    performing an image processing for the initial image to generate the output image whose data size is less than a data size of the initial image.

3. The method according to claim 1, further comprising: transmitting the recognized matching result to a memory of the terminal device by the cloud server; and receiving the recognized matching result by the memory of the terminal device.

4. The method according to claim 3, further comprising: transmitting a corrected information regarding an actual measurement value or/and an actual measurement unit to the cloud server by the terminal device after receiving the recognized matching result from the cloud server.

5. The method according to claim 1, further comprising: performing a unit conversion process for the recognized matching result to generate a converted matching result by the cloud server; and storing the converted matching result by the cloud server.

6. The method according to claim 1, wherein the recognized measurement value is a first recognized measurement value, the recognized measurement unit is a first recognized measurement unit, the recognized matching result is a first recognized matching result, and the method further comprises recognizing the output image to obtain a second recognized matching result which is related to a second recognized measurement value and a second recognized measurement unit and storing the second recognized matching result by the cloud server.

7. A method for processing a physiological image information comprising:
    taking a measurement result image of a physiological measurement device by a camera of a terminal device to generate an output image;
    transmitting the output image to a cloud server by a communication interface of the terminal device;
    recognizing the output image to obtain a recognized matching result having a recognized physiological state value and a recognized physiological state unit by the cloud server;
    transmitting the recognized matching result to the terminal device by the cloud server to generate a confirmed matching result regarding a confirmed physiological state value and a confirmed physiological state unit;
    transmitting the confirmed matching result to the cloud server by the terminal device;
    storing the confirmed matching result by the cloud server; and
    comparing physiological state information and a personal state interval by the cloud server, and transmitting a warning message to the terminal device or a user application interface by the cloud server when the physiological state information is outside the personal state interval, wherein the personal state interval is related to daily routine, medication record, or medical history of a user.

8. The method according to claim 7, further comprising instructing the cloud server to share the confirmed physiological state value and the confirmed physiological state unit to a user application interface by the terminal device.

9. The method according to claim 7, further comprising transmitting a health education request to the cloud server by the terminal device or a user application interface;
and transmitting a health education information to the terminal device or the user application interface according to the health education request by the cloud server.

10. The method according to claim 7, wherein storing the confirmed matching result by the cloud server comprises:
storing the confirmed physiological state value and the confirmed physiological state unit by the cloud server; and
updating a historical physiological state record table or a historical physiological state tendency chart according to the confirmed physiological state value and the confirmed physiological state unit by the cloud server.

11. The method according to claim 10, further comprising: instructing the cloud server to share the historical physiological state record table or the historical physiological state tendency chart to a user application interface.

12. The method according to claim 10, wherein the confirmed physiological state value is a first confirmed physiological state value, the confirmed physiological state unit is a first confirmed physiological state unit, the confirmed matching result is a first confirmed matching result, the method for processing the physiological image information further comprises:
recognizing the output image by the cloud server to obtain a second recognized matching result regarding a second recognized physiological state value and a second recognized physiological state unit;
transmitting the second recognized matching result to the terminal device to obtain a second confirmed matching result regarding a second confirmed physiological state value and a second confirmed physiological state unit;
transmitting the second confirmed matching result to the cloud server by the terminal device; and
storing the second confirmed matching result by the cloud server.

13. The method according to claim 12, wherein the historical physiological state record table is a first historical physiological state record table, the historical physiological state tendency chart is a first historical physiological state tendency chart, storing the second confirmed matching result by the cloud server comprises:
storing the second confirmed physiological state value and the second confirmed physiological state unit by the cloud server; and
updating a second historical physiological state record table or a second historical physiological state tendency chart according to the second confirmed physiological state value and the second confirmed physiological state unit by the cloud server.

14. The method according to claim 13, further comprising combining the first historical physiological state record table and the second historical physiological state record table to create a comprehensive historical physiological state record table or combining the first historical physiological state tendency chart and the second historical physiological state tendency chart to create a comprehensive historical physiological state tendency chart by the cloud server.

15. The method according to claim 10, wherein the physiological measurement device is a first physiological measurement device, the measurement result image is a first measurement result image, the output image is a first output image, and the recognized physiological state value is a first recognized physiological state value, the recognized physiological state unit is a first recognized physiological state unit, the recognized matching result is a first recognized matching result, the confirmed physiological state value is a first confirmed physiological state value, the confirmed physiological state unit is a first confirmed physiological state unit, the confirmed matching result is a first confirmed matching result, the method for processing a physiological image information comprises:
taking a second measurement result image of a second physiological measurement device by the camera to generate a second output image;
transmitting the second output image to the cloud server by the communication interface;
recognizing the second output image by the cloud server to obtain a second recognized matching result regarding a second recognized physiological state value and a second recognized physiological state unit;
transmitting the second recognized matching result to the terminal device by the cloud server to generate a second confirmed matching result regarding a second confirmed physiological state value and a second confirmed physiological state unit;
transmitting the second confirmed matching result to the cloud server by the terminal device; and
storing the second confirmed matching result by the cloud server.

16. The method according to claim 15, wherein the historical physiological state record table is a first historical physiological state record table, the historical physiological state tendency chart is a first historical physiological state tendency chart, and storing the second confirmed matching result by the cloud server comprising:
storing the second confirmed physiological state value and the second confirmed physiological state unit by the cloud server; and
updating a second historical physiological state record table or a second historical physiological state tendency chart according to the second confirmed physiological state value and the second confirmed physiological state unit by the cloud server.

17. The method according to claim 16, further comprising combining the first historical physiological state record table and the second historical physiological state record table to create a comprehensive historical physiological state record table or combining the first historical physiological state tendency chart and the second historical physiological state tendency chart to create a comprehensive historical physiological state tendency chart by the cloud server.

18. An equipment for processing physiological image information comprising:
a terminal device comprising a camera and a communication interface electrically connected to the camera, with the camera configured to photograph a measurement result image of a measurement device to generate an output image; and
a cloud server electrically connected to the communication interface, with the cloud server configured to recognize the output image to obtain a recognized matching result having a recognized measurement value and a recognized measurement unit, and with the cloud server storing the recognized matching result and transmitting the recognized matching result to the terminal device, wherein the cloud server further compares physiological state information and a personal state interval, and transmits a warning message to the terminal device or a user application interface when the physiological state information is outside the personal state interval, wherein the personal state interval is related to daily routine, medication record, or medical history of a user.

19. The equipment according to claim 18, wherein the terminal device further comprises a display screen that is electrically connected to the camera, the display screen is configured to display a frame and a direction indicator, the measurement result image is displayed in the frame, and the direction indicator is outside the frame.

* * * * *